United States Patent [19]

Friauf et al.

[11] Patent Number: 5,435,307
[45] Date of Patent: Jul. 25, 1995

[54] SURFACE FLUORESCENT MONITOR

[75] Inventors: Walter S. Friauf, Bethesda; Paul D. Smith, Annapolis; John W. Cole, Rockville; Joseph F. Fessler, Walkersville, all of Md.; Roger E. Solomon, Manassas, Va.; Eric F. Bernstein, Philadelphia, Pa.

[73] Assignee: The United States of America as represented by the Secretary of the Department of Health and Human Services, Washington, D.C.

[21] Appl. No.: 676,581

[22] Filed: Mar. 29, 1991

[51] Int. Cl.⁶ .................................. A61B 5/00
[52] U.S. Cl. ................................ 128/633; 128/634; 128/665
[58] Field of Search ........................ 128/664–666, 128/633–634; 356/41

[56] References Cited

U.S. PATENT DOCUMENTS

| | | | |
|---|---|---|---|
| 3,980,434 | 9/1976 | Mertz . | |
| 3,992,631 | 11/1976 | Harte . | |
| 4,071,020 | 1/1978 | Pugliese . | |
| 4,476,870 | 10/1984 | Peterson et al. | 128/666 |
| 4,539,180 | 9/1985 | Schwartz . | |
| 4,559,299 | 12/1985 | Rotman . | |
| 4,608,990 | 1/1986 | Elings | 128/666 |
| 4,694,833 | 9/1987 | Hamaguri | 128/633 |
| 4,782,819 | 11/1988 | Adair | 128/665 |
| 4,877,872 | 10/1989 | Morgan et al. . | |
| 4,920,143 | 4/1990 | Levy et al. . | |
| 4,925,736 | 4/1990 | Shikowitz . | |
| 4,968,715 | 11/1990 | Dougherty et al. . | |
| 5,047,627 | 9/1991 | Yim et al. | 128/634 |
| 5,094,239 | 3/1992 | Jaeb et al. | 128/633 |
| 5,096,671 | 3/1992 | Kane et al. | 128/634 |
| 5,119,814 | 6/1992 | Minnich | 128/666 |

Primary Examiner—Lee S. Cohen
Assistant Examiner—Robert L. Nasser, Jr.
Attorney, Agent, or Firm—Lowe, Price, LeBlanc & Becker

[57] ABSTRACT

A method of optimizing photodynamic therapy in which retained concentrations of photosensitizers administered are measured on a real time basis by percutaneous measurements of fluorescence. A light weight hand held fluorometer is used to percutaneously measure fluorescence emitted by photosensitizers in a tissue situs that is subject to photodynamic therapy. The use of real time determinations of the concentration of photosensitizers allow optimization of illumination intensity and duration.

5 Claims, 3 Drawing Sheets

SURFACE FLUORESCENT MONITOR

TECHNICAL FIELD

The present invention relates to the field of photodynamic therapy. More particularly, the present invention relates to a hand held fluorometer and a method of surface fluorescent monitoring in which tissue concentration of photosensitizers is determined by transcutaneous fluorescent measurements.

BACKGROUND ART

Photodynamic therapy (PDT) involves the use of light of an appropriate wavelength to excite an administered photosensitizer resulting in tissue destruction. A purified form of hematoporphyrin derivative (HPD), high in dihematoporphyrin ethers/esters, (DHE), is the photosensitizer most frequently used in PDT. HPD and DHE are selectively retained in tumors allowing for tumor destruction while sparing normal structures during PDT. This process is distinct from psoralen-based light therapy commonly used in dermatology. Cutaneous disorders are particularly well suited to PDT because their accessibility allows for adequate light administration. Basal cell carcinoma, squamous cell carcinoma, melanoma, mycosis fungoides, Kaposi's sarcoma, metastatic breast carcinoma, and Bowen's disease all have been treated with PDT using HPD or DHE.

Photodynamic effect is a function of 4 variables: the light dose given, tissue DHE content, melanin and other substances competing with DHE for light absorption, and tissue oxygen content. Light delivery is usually accomplished with an argon or argon-pumped dye laser and may be closely controlled for total light dose and treatment area. Since PDT requires oxygen to exert a cytocidal effect, hypoxic tissues are relatively resistant to treatment with PDT.

Tissue DHE content is a function of the administered dose of DHE and retention within various tissues. Different tissues and tumors retain varying amounts of DHE. Individual variations in retention and excretion of DHE may result in differences in DHE content in similar individuals. Currently, tissue and tumor DHE are estimated based on the amount of DHE administered. By overestimating tumor DHE content, inadequate light may be administered which subsequently results in decreased tumoricidal effect. An underestimation of DHE present may result in over treatment of normal structures with the result being unacceptable normal tissue destruction. In addition, measurements of target and normal tissue DHE may be made repeatedly over time as DHE is cleared. Thus, light delivery should be timed to coincide with maximal target tissue retention of DHE over normal structures. A quicker method of measuring relative tissue DHE content would allow for more accurate light dosing, optimizing PDT.

The present invention provides for a non-invasive method and apparatus for accurately measuring the relative amount of tissue DHE content.

DISCLOSURE OF THE INVENTION

It is accordingly one object of the present invention to provide a method of non-invasively measuring the relative amount of a photosensitizer present in a tissue situs.

Another object of the present invention is to provide a method of determining the relative amount of a photosensitizer present in a tissue situs which utilizes transcutaneous fluorescent measurements.

A further object of the present invention is to provide a method of optimizing photodynamic therapy.

A still further object of the present invention is to provide a fluorometer for transcutaneously measuring the relative amount of a photosensitizer present in a tissue situs.

A still further object of the present invention is to provide a compact, light weight, hand held fluorometer for transcutaneously measuring the relative amount of a photosensitizer present in a tissue situs.

According to these and other objects of the present invention which will become apparent as the description thereof is presented below, there is provided by the present invention a hand held fluorometer which includes:

a housing having a conical portion;

an optical fiber for directing illumination of a first predetermined excitation wavelength to the conical portion and out an opening in the conical portion;

a first sensor positioned in the conical portion for measuring illumination of a second predetermined emittance wavelength which enters the opening in the conical portion;

filter means positioned between the first sensor and the opening for passing only light of said second predetermined wavelength to the first sensor;

electrical circuitry contained in the housing for receiving a signal from the first sensor and converting the received signal into an a.c. signal; and electrical connectors located through the housing and connected to receive the a.c. signal from the electrical circuit.

Also provided by the present invention is a method of photodynamic therapy which includes sequential steps of;

administering a dosage of a photosensitizer to a subject;

measuring the concentration of the photosensitizer in a predetermined tissue situs; and exciting the photosensitizer in the tissue situs by applying light thereto of a sufficient wavelength to cause the excitation of the photosensitizer.

BRIEF DESCRIPTION OF THE DRAWINGS

The present invention will now be described with reference to the annexed drawings, which are given by way of a non-limiting examples in which.

BEST MODE FOR CARRYING OUT THE INVENTION

According to the present invention, tissue DHE is measured transcutaneously by a hand held fluorometer. In utilizing the hand held fluorometer, pulsed laser light is delivered through a fiber optics system to a small area of the skin. Resulting tissue fluorescence is measured by photo diodes. According to the present invention, it has been discovered that skin fluorescence is a function of tissue DHE content as well as background tissue fluorescence. Thus, readings are expressed relative to those of normal skin containing no DHE. As discussed in more detail below, the apparatus of the present invention can operate in a self calibration mode to allow for standardization of data runs.

Transcutaneous measurements of skin fluorescence according to the present invention were found to correlate well with given DHE dose and tissue extraction determinations of DHE. Although tissue extraction determinations of DHE content offer accurate measurements of tissue DHE, such methods require tissue biopsy and procedures which take hours to obtain results. Moreover, since tissue DHE content changes as a function of time, this method has limited clinical utility and cannot provide real-time estimates of tissue DHE. In contrast, transcutaneous fluorometric determination of DHE content according to the present invention provides for accurate real-time estimates of tissue DHE, which allows for more accurate light delivery thus, optimizing PDT.

The hand held fluorometer of the present invention includes a housing which houses an illuminating fiber optics system which delivers light of a suitable wavelength, e.g, 450 to 500 nm, from an argon laser source to an area of the skin. The housing also includes photo diodes which receive tissue fluorescence.

Figure 1:
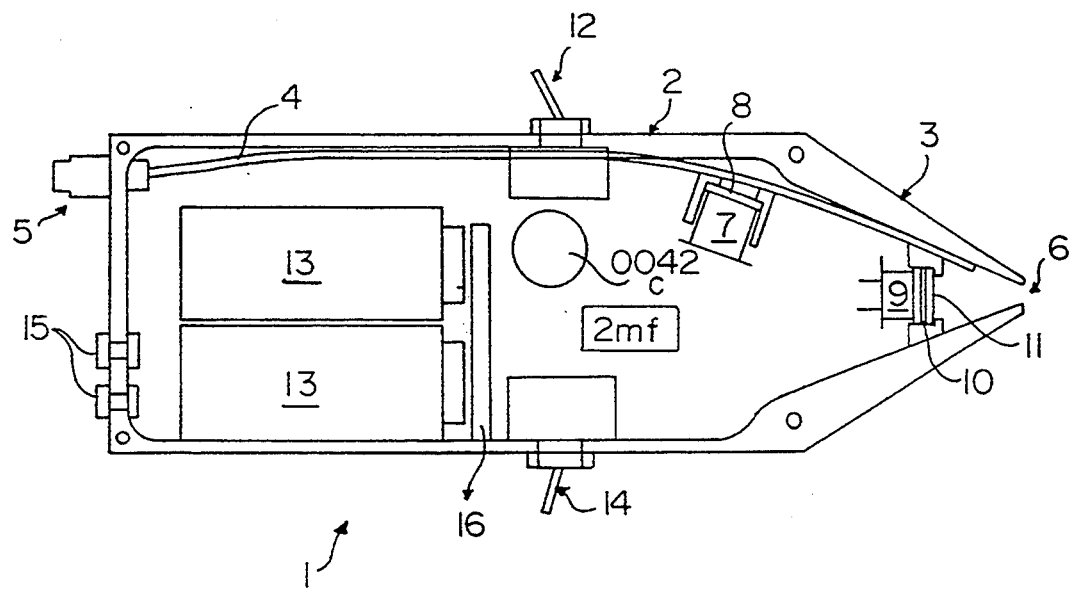
FIG. 1 is a schematic diagram illustrating the basic elements of the hand held fluorometer according to one embodiment of the present invention.

FIG. 1 is a schematic diagram illustrating the basic elements of the hand held fluorometer according to one embodiment of the present invention. As depicted in FIG. 1, the hand held fluorometer device of the present invention, generally labelled 1, includes a housing 2 which has a conical end portion 3, discussed in more detail below. Other than the conical end portion 3, the remaining portion of the housing may be of any convenient cross sectional shape such as rectangular (illustrated), cylindrical, etc. Moreover, the housing may incorporate an appropriate shape for gripping the device by hand.

The housing 2 contains an optical fiber system which includes a length of optical fiber 4 which is connected at one end to a standard optical fiber coupler 5 fixed through one side or end portion of the housing 2. The other end of optical fiber 4 is positioned in the conical portion of the housing 3, so as to direct light of an excitation wavelength through an opening 6 in the end of the conical portion of the housing. The opening 6 may be covered with a suitable window or lens element which does not interfere with the excitation or emittance wavelengths utilized.

In operation, light from a laser, e.g., an argon laser is fed to optical fiber 4 through an optical fiber which is externally attached to connector 5. In order to monitor the intensity of the excitation illumination, a minute but fixed fraction of the light in the optical fiber escapes and is monitored by a secondary sensor 7, e.g., a silicon photo diode. As illustrated in FIG. 1, a filter 8 which passes only excitation light at a predetermined wavelength, e.g. about 488 nm for DHE, is placed over secondary sensor 7 to insure that the secondary sensor 7 monitors only excitation light.

The secondary sensor 7 may be switched into the operation circuit as needed to monitor the intensity of the illumination, which may not always be the same. This reading taken by the secondary sensor 7 may be utilized to normalize subsequent fluorescent readings in a conventional manner.

Fluorescence is detected by a primary sensor 9, e.g., a silicon photo diode, which is positioned near and in alignment with the opening 6 in the conical portion of the housing 3 as illustrated. A filter 10 which passes only fluorescence of a photosensitizer of interest, e.g., red for DHE, is place over the primary sensor, a second filter 11 which blocks excitation wavelength is also placed over the primary sensor 9. This additional filter 11 allows fluorescence of a selected photosensitizer, e.g. DHE, to be read with a minimum of self florescence.

An important feature of the device is the conical sensing head which localizes and standardizes measurements. The shape of the conical portion of the housing 3 and size of the opening 6 should provide for measuring fluorescence on an area of the skin which is about 0.25 $cm^2$, or less. In this regard, an opening having a diameter of about 2 mm or less was found to be particularly well suited for purposes of the present invention. Although areas as large as 1 $cm^2$ could be used, smaller areas eliminate background interference and make standardization more accurate. In some embodiments of the device the illumination fiber may be brought outside of the conical sensing head in order to reduce background reading caused by fluorescence of the optical filters or possibly by residual broadband plasma glow in the laser within the housing, at the expense of some degradation of standardization.

The housing contains a power switch 12 which connects power from one or more batteries 13 within the housing to the operational circuit described below. For illustrative purposes two nine volt batteries are shown in FIG. 1. As illustrated in FIG. 1 the batteries are preferably contained by a suitable barrier 16. The housing also contains a calibration switch 14 which connects the secondary sensor 7 to the operational circuit which monitors stray light leaking from optical fiber 4 in the housing for normalizing the reading as discussed above. By normalizing the readings it is not necessary to know the exact output of the laser.

Signals from the sensors are processed by the internal amplifying circuit and feed to electrical connectors 15, e.g., pin connectors. In operation, a suitable read out device, which is separate from the hand held fluorometer is connected to the electrical connectors 14 in a known manner. The preferred readout device utilized is a multi-meter (e.g., Model 24S, Data Precision Corp., Wakefield, Mass.); however, other devices such as an oscilloscope, a lock-in amplifier, or the like could be used. The readout device is purposely kept remote so as to keep the hand held unit small and light, and to avoid any interference from stray light.

Not illustrated is an embodiment in which the necessary illumination light may be provided for by light emitting diodes contained within the housing member.

Figure 2:
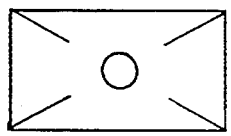
FIG. 2 is a schematic diagram of the hand held fluorometer of FIG. 1 illustrating the cross sectional shape of the housing.

FIG. 2 is a schematic diagram of the hand held fluorometer of FIG. 1 illustrating the cross sectional shape of the housing. As illustrated in FIG. 2, the housing 2 can have a rectangular cross section. However, as noted above, any convenient cross sectional shape such as rectangular (illustrated), cylindrical, etc. may be utilized. Moreover, the housing may incorporate an appropriate shape for gripping the device by hand. FIG. 2 also illustrates the conical portion of the housing 3 and the opening 6. The conical portion of the housing is referred to as the front portion of the device.

Figure 3:
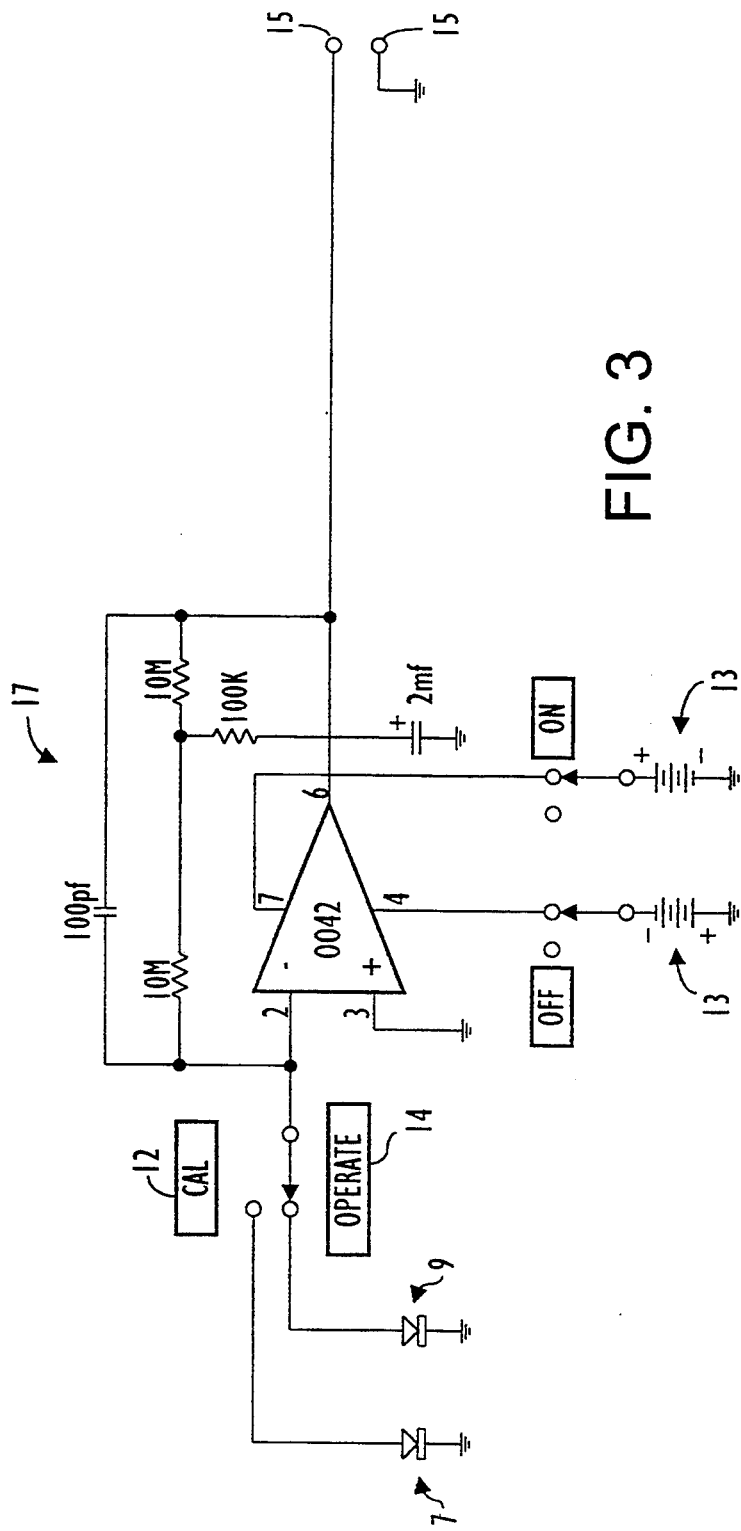
FIG. 3 is a schematic diagram illustrating the electrical circuitry of the hand held fluorometer according to one embodiment of the present invention.

FIG. 3 is a schematic diagram illustrating the electrical circuitry of the hand held fluorometer according to one embodiment of the present invention. As illustrated in FIG. 3, the electrical circuitry includes a standard high gain amplifier 17 which is a.c. coupled to minimize trouble from drift and stray light, and which contains several standard components to prevent oscillation at high frequencies, and to limit the band width to the fundamental frequency of the excitation light. In operation utilizing a laser with a chopper as the illumination source, the signal from the sensors is electrically filtered by a band pass filter centered on the chopped frequency, and amplified by the high gain a.c. amplifier.

The following example is presented to illustrate the invention which is not intended to be considered as being limited thereto.

EXAMPLE

Female strain 2/NCR guinea pig (350–500 g) were used. Hair removal was accomplished 24 hours after photosensitizer administration by shaving and subsequent application of a depilatory lotion. The depilatory lotion was allowed to dry for 15 minutes then was removed with warm water. Hair removal was completed with little or no erythema. Depilation was accomplished 24 hours prior to fluorescent measurements and harvesting of skin samples. Hair removal, light treatment, and skin biopsy were carried out after anesthesia with intraperitoneal ketamine hydrochloride (90 mg/kg) and xylazine hydrochloride (2 mg/kg). Guinea pigs were housed in reduced lighting and shielded from direct light from the time of photosensitizer administration until euthanasia.

The photosensitizer utilized in this example was Photofrin (Quadra Logic Tech., Vancouver, Canada), a brand of dihematoporphyrin esters (DHE) which is a purified product of hematoporphyrin derivative (HPD). The Photofrin was diluted in an isotonic saline solution at a concentration of 2.5 mg/ml.

Photodynamic therapy was conducted utilizing blue light at a wavelength of 488 nm. The light was delivered using an argon laser (model PRT 100, Coherent, Inc., Palo Alto, Calif.) coupled to a 600 micron, fused silica, flat end optical fiber (model PCS 600, Q.P.C., Inc., Plainfield, N.J.).

The hand held fluorometer utilized in this example is described in detail above. An argon laser delivered 488 nm light to the illuminating fiber optics. Illuminating light was chopped at 6 hertz, this being the lowest frequency at which most multi-meters will read correctly on their a.c. ranges. The power level of the excitation light was 25 mw delivered over an area of about 0.25 $cm^2$, or about 100 mw/$cm^2$.

Standard disposable 4 mm skin punches were used to remove tissue samples from anesthetized animals for skin DHE determination. Fat was trimmed from the biopsy samples. Samples were weighed and then lyophilized overnight. After homogenization of tissue using glass hand held homogenizers, DHE was extracted by acid extraction and tissue sonicated. The extract was spun in a centrifuge at 5000 rpm for 5 minutes to remove cellular debris, and DHE fluorescence was then determined using a Fluorescence Spectrofluorometer LS-5 (Perkin-Ellmer, Norwalk, Conn.). An excitation wavelength of 395 nm and an emission wavelength of 609 nm was used and expressed per weight of fresh tissue. Fluorescence values for tissue obtained as above were compared to fluorescence tissue containing no DHE.

Figure 4:
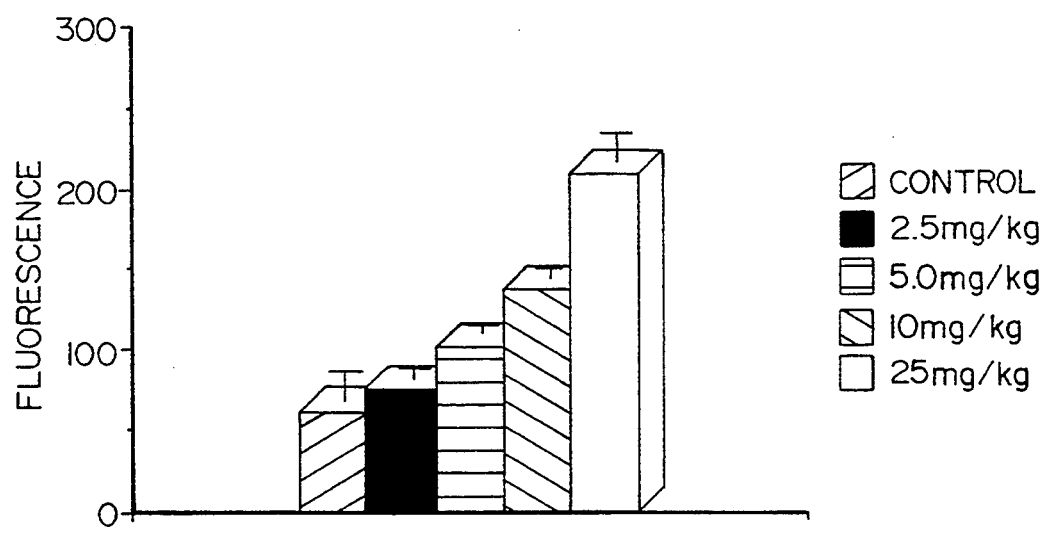
FIG. 4 is a bar graph which compares fluorescence as a function of photosensitizer dosage for the method of the present invention.

Readings of tissue fluorescence were measured at sites on the backs of each guinea pig near the midline. Two to four readings were made on each animal. Sites were chosen on white skin and were at least 3 cm apart. Since the guinea pigs were bi-colored, the number of readings depended on the amount of white skin on each animal. All guinea pigs showed statistically significant ($p<0.05$) differences in fluorescence, with the exception of the lowest DHE dose of 2.5 mg/kg verses the control guinea pig which received no DHE (FIG. 4). Although the mean fluorescence measured in the guinea pig receiving 2.5 mg/kg of DHE was larger than that of the control animal, this difference was not statistically significant ($p=0.4$).

Figure 5:
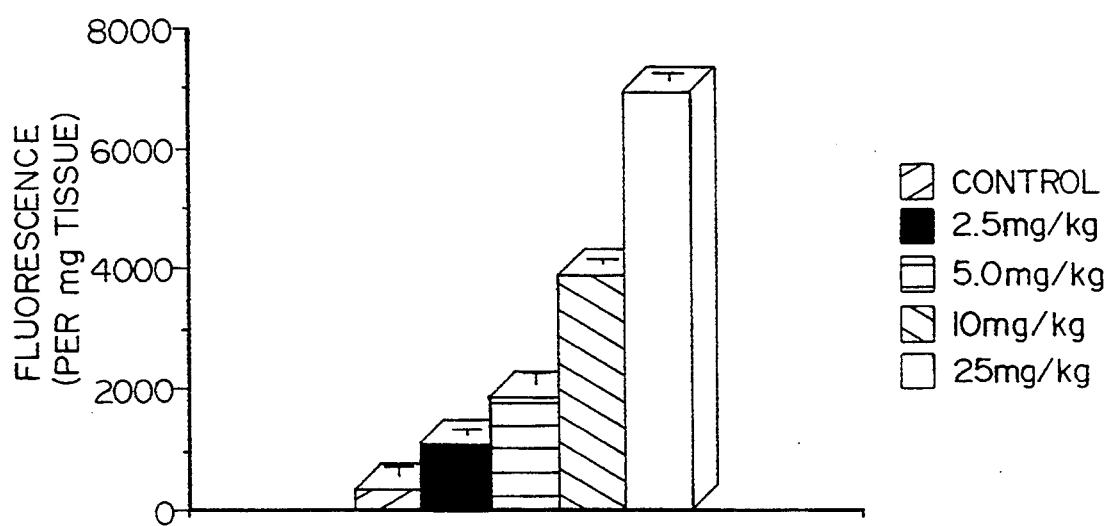
FIG. 5 is a bar graph which compares fluorescence as a function of photosensitizer dosage for a tissue extraction method.

Fluorescence of tissue biopsy specimens correlated well with given DHE dose. Values increased incrementally from the control animal receiving no DHE to the highest DHE dose of 25 mg/kg (FIG. 5). Differences were statistically significant at the $p<0.01$ level. Tissue biopsy fluorescent measurements were a more sensitive predictor of tissue DHE content than transcutaneous measurements. However, either method was able to distinguish between all given doses of DHE.

Determination of DHE content in guinea pig skin by tissue biopsy and subsequent DHE extraction correlated well with given DHE dose. All guinea pigs showed statistically significant differences in fluorescence. Fluorometer readings also correlated well with given DHE dose. Although there is evidence that the tissue extraction method of DHE skin content allows for more precise differentiation of doses than the transcutaneous measurement via the fluorometer, its clinical utility is seriously limited inasmuch as this method requires many hours to arrive at a reading, and requires a tissue biopsy. A tissue biopsy itself may alter tissue oxygenation and optical properties thus affecting PDT in an unknown manner. Transcutaneous florescence allows for instantaneous tissue PDT estimates and uses minimal amounts of light. Light doses used are well below tissue threshold for PDT induced damage.

In most clinical settings the appropriate light dose to administer is estimated by considering the given DHE dose and previous experience. While various tissues retain DHE to different degrees, individual variation in processing of DHE may also account for variation in DHE retention between individuals. Although McCullough et al were able to achieve selective destruction of psoriatic plaques with PDT, they suggest that either changing the amount of DHE or light administered would eliminate overtreatment of Lesions (McCullough et al, "Photosensitizers in Dermatology", *Photochem Photobiol.* 46: 77–82 (1987)). Bandieramonte et al hand a favorable response in 75% of cutaneous and subcutaneous neoplasms. They experienced overtreatment of some lesions with difficulty in healing of resulting wounds (Bandieramonte et al, "Laser Phototherapy Following HpD Administration in Superficial Neoplastic Lesions" *Tumori* 70: 327–334 (1984)). While overtreatment of lesions may cause undesirable toxicity, undertreatment may result in tumor recurrence. Knowledge of tissue DHE content would allow for optimization of PDT, thereby maximizing target tissue toxicity while minimizing destruction of surrounding normal tissue.

Melanin content of target tissue and normal structures may effect the amount of light necessary to produce cytotoxicity. When reading tissue DHE content via the present hand held fluorometer, the wavelength of the excitation beam was selected to be the same as that of the treatment beam. Competing chromophores such as melanin would absorb the excitation beam of the fluorometer to the same extent as the treatment beam. Thus, individual and tissue variations in melanin content are reflected in fluorescence readings, thereby adjusting for pigmentation.

As PDT is optimized by utilizing newer dyes with increased tumor selectivity, better light delivery systems, and accurate methods of determining tissue DHE content, an increasing number of conditions will be amenable to treatment by this modality. The fluorometer of the present invention enables real-time estimates of tissue DHE, which will allow more accurate light delivery, thus improving PDT. Application of the fluorometer and method of the present invention to psoralen-based light therapy enables instantaneous determinations of skin psoralen content, obviating the need for minimal erythema dose (MED) determinations currently used when delivering psoralen/ultraviolet A, or PUVA, therapy. Cutaneous disorders are particularly well suited to PDT according to the present invention because their accessibility allows for adequate light administration. Basal cell carcinoma, squamous cell carcinoma, melanoma, mycosis fungoides, Kaposi's sarcoma, metastatic breast carcinoma, and Bowen's disease can all be treated with PDT using HPD or DHE according to the present invention.

Although the invention has been described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims that follow.

What is claimed is

1. A hand held fluorometer comprising:
   a housing having a conical portion;
   an optical fiber connector located in a wall of said housing for connecting said hand held fluorometer to an external source of light;
   an optical fiber within said housing which is connected to said connector for directing illumination of a first predetermined excitation wavelength from the external source of light to said conical portion and out an opening in said conical portion;
   a first sensor positioned in said conical portion for measuring illumination of a second predetermined fluorescent wavelength which enters said opening in said conical portion;
   filter means positioned between said first sensor and said opening for passing only light of said second predetermined fluorescent wavelength to said first sensor;
   electrical circuitry contained in said housing and connected to said first sensor for receiving a signal from said first sensor and converting said received signal into an a.c. signal;
   electrical connectors located through said housing and connected to receive said a.c. signal from said electrical circuitry;
   a second sensor positioned along a side of said optical fiber for monitoring light of said first predetermined excitation wavelength which is directed from said optical fiber through said opening in said conical portion of said housing;
   filter means positioned between said second sensor and said optical fiber for passing only light of said first predetermined excitation wavelength to said second sensor; and
   a calibration circuit which includes said second sensor and a switch means to selectively connect said first and said second sensor to said electrical circuitry.

2. A hand held fluorometer according to claim 1, wherein said first and second sensors comprise photo diodes.

3. A hand held fluorometer according to claim 1 further comprising an internal power supply for said electrical circuitry.

4. A hand held fluorometer according to claim 1, wherein said electrical circuitry comprises a high gain a.c. amplifier.

5. A hand held fluorometer according to claim 1, wherein said opening is about 2 mm in diameter.

* * * * *